United States Patent
Kudou et al.

(10) Patent No.: US 7,807,854 B2
(45) Date of Patent: Oct. 5, 2010

(54) EFFECTIVE USE METHOD OF MEDICAMENTS AND METHOD OF PREVENTING EXPRESSION OF SIDE EFFECT

(75) Inventors: Shinji Kudou, Tochigi (JP); Kazuhiko Kuriyama, Tochigi (JP); Tokutarou Yasue, Ibaraki (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/650,899

(22) Filed: Dec. 31, 2009

(65) Prior Publication Data

US 2010/0099606 A1    Apr. 22, 2010

Related U.S. Application Data

(62) Division of application No. 11/631,128, filed as application No. PCT/JP2005/013113 on Jul. 15, 2005, now Pat. No. 7,781,617.

(30) Foreign Application Priority Data

Jul. 16, 2004  (JP) ............................. 2004-209591
Mar. 2, 2005   (JP) ............................. 2005-056875

(51) Int. Cl.
C07C 217/34   (2006.01)
C07C 217/56   (2006.01)
C07C 217/64   (2006.01)
C07C 255/54   (2006.01)
C07C 317/22   (2006.01)
C07C 317/32   (2006.01)
C07C 323/32   (2006.01)
A61P 37/06    (2006.01)

(52) U.S. Cl. .................. 564/336; 564/341; 564/346; 564/348; 564/351; 564/360; 564/374; 546/334; 514/357; 514/651; 514/653

(58) Field of Classification Search .................. None
See application file for complete search history.

(56) References Cited

U.S. PATENT DOCUMENTS

| | | | |
|---|---|---|---|
| 5,447,922 A | 9/1995 | Lawrence et al. | |
| 5,604,229 A | 2/1997 | Fujita et al. | |
| 5,948,820 A | 9/1999 | Fujita et al. | |
| 6,004,565 A | 12/1999 | Chiba et al. | |
| 6,214,873 B1 | 4/2001 | Adachi et al. | |
| 6,489,331 B1 | 12/2002 | Shimada et al. | |
| 6,960,692 B2 * | 11/2005 | Kohno et al. | 564/341 |
| 6,963,012 B2 | 11/2005 | Kohno et al. | |
| 7,456,157 B2 | 11/2008 | Kohno et al. | |
| 7,482,491 B2 | 1/2009 | Kohno et al. | |
| 2002/0040050 A1 | 4/2002 | Xu et al. | |
| 2002/0091105 A1 | 7/2002 | Mandala et al. | |
| 2002/0143034 A1 | 10/2002 | Taniguchi et al. | |
| 2003/0236297 A1 | 12/2003 | Nishi et al. | |
| 2004/0058894 A1 | 3/2004 | Doherty et al. | |
| 2004/0067908 A1 | 4/2004 | Nakade et al. | |
| 2004/0087662 A1 | 5/2004 | Bigaud et al. | |
| 2004/0110728 A1 | 6/2004 | Macdonald et al. | |
| 2004/0138462 A1 | 7/2004 | Sakurai et al. | |
| 2004/0147490 A1 | 7/2004 | Albert et al. | |
| 2004/0224941 A1 | 11/2004 | Seko et al. | |
| 2004/0235794 A1 | 11/2004 | Nakade et al. | |
| 2004/0242654 A1 | 12/2004 | Kohno et al. | |
| 2004/0248952 A1 | 12/2004 | Pan et al. | |
| 2004/0254222 A1 | 12/2004 | Kohno et al. | |
| 2005/0009786 A1 | 1/2005 | Pan et al. | |
| 2005/0020837 A1 | 1/2005 | Doherty et al. | |
| 2005/0033055 A1 | 2/2005 | Bugianesi et al. | |
| 2005/0043386 A1 | 2/2005 | Nishi et al. | |
| 2005/0107345 A1 | 5/2005 | Doherty et al. | |
| 2005/0222422 A1 | 10/2005 | Lynch et al. | |
| 2005/0245575 A1 | 11/2005 | Chen et al. | |
| 2006/0046979 A1 | 3/2006 | Foster et al. | |
| 2006/0089334 A1 | 4/2006 | Budhu et al. | |
| 2006/0135622 A1 | 6/2006 | Kohno et al. | |
| 2006/0135786 A1 | 6/2006 | Saha et al. | |
| 2006/0148830 A1 | 7/2006 | Terakado et al. | |
| 2006/0148844 A1 | 7/2006 | Nakade et al. | |

(Continued)

FOREIGN PATENT DOCUMENTS

JP    11-080026    3/1999

(Continued)

OTHER PUBLICATIONS

Blam et al., Integrating Anti-Tumor Necrosis Factor Therapy in Inflammatory Bowel Disease: Current and Future Perspectives, Am. J. Gastroenterology, 2001, vol. 96, No. 7, pp. 1977-1997.

(Continued)

*Primary Examiner*—Brian J Davis
(74) *Attorney, Agent, or Firm*—Wenderoth, Lind & Ponack, L.L.P.

(57) ABSTRACT

To provide a medicament which efficiently expresses an immunosuppressive agent or an anti-inflammatory agent and reduces expression of side effect.

A medicament includes diaryl sulfide or diaryl ether compound having a 2-amino-1,3-propanediol structure having an activity of reducing lymphocytes circulating peripherally, in combination with an immunosuppressive agent and/or an anti-inflammatory agent.

7 Claims, 2 Drawing Sheets

U.S. PATENT DOCUMENTS

| | | |
|---|---|---|
| 2006/0160771 A1 | 7/2006 | Kohno et al. |
| 2006/0161005 A1 | 7/2006 | Doherty et al. |
| 2006/0166940 A1 | 7/2006 | Buehlmayer et al. |
| 2006/0211656 A1 | 9/2006 | Albert et al. |
| 2006/0211658 A1 | 9/2006 | Hinterding et al. |
| 2006/0252741 A1 | 11/2006 | Colandrea et al. |
| 2006/0264403 A1 | 11/2006 | Albert |
| 2007/0010494 A1 | 1/2007 | Ehrhardt et al. |
| 2007/0043014 A1 | 2/2007 | Doherty et al. |
| 2007/0088002 A1 | 4/2007 | Lynch et al. |
| 2007/0135501 A1 | 6/2007 | Hinterding et al. |
| 2007/0149597 A1 | 6/2007 | Nishi et al. |
| 2007/0167410 A1 | 7/2007 | Pan et al. |
| 2007/0167425 A1 | 7/2007 | Nakade et al. |
| 2007/0191468 A1 | 8/2007 | Nishi et al. |
| 2007/0203100 A1 | 8/2007 | Pan et al. |
| 2007/0225260 A1 | 9/2007 | Hinterding et al. |
| 2008/0025973 A1 | 1/2008 | Fleenor et al. |
| 2008/0027508 A1 | 1/2008 | Chu |
| 2008/0032923 A1 | 2/2008 | Kudou et al. |
| 2008/0153882 A1 | 6/2008 | Nishi et al. |
| 2008/0161410 A1 | 7/2008 | Kusters et al. |
| 2008/0200438 A1 | 8/2008 | Albert et al. |
| 2008/0207584 A1 | 8/2008 | Habashita et al. |
| 2008/0207941 A1 | 8/2008 | Tsubuki et al. |
| 2008/0249093 A1 | 10/2008 | Colandrea et al. |
| 2009/0023797 A1 | 1/2009 | Azzaoui et al. |

FOREIGN PATENT DOCUMENTS

| | | |
|---|---|---|
| JP | 2002-53575 | 2/2002 |
| JP | 2002-316985 | 10/2002 |
| JP | 2003-137894 | 5/2003 |
| JP | 2003-267936 | 9/2003 |
| JP | 2004-137208 | 5/2004 |
| JP | 2004-307439 | 11/2004 |
| JP | 2004-307440 | 11/2004 |
| JP | 2004-307441 | 11/2004 |
| JP | 2004-307442 | 11/2004 |
| JP | 2005-47899 | 2/2005 |
| JP | 2005-247691 | 9/2005 |
| WO | 01/98301 | 12/2001 |
| WO | 02/067915 | 9/2002 |
| WO | 02/100148 | 12/2002 |
| WO | 03/029184 | 4/2003 |
| WO | 03/029205 | 4/2003 |
| WO | 2005/014525 | 2/2005 |
| WO | 2005/014603 | 2/2005 |
| WO | 2005/063671 | 7/2005 |
| WO | 2006/041015 | 4/2006 |
| WO | 2006/063033 | 6/2006 |
| WO | 2006/129688 | 12/2006 |
| WO | 2007/043433 | 4/2007 |
| WO | 2007/043568 | 4/2007 |
| WO | 2007/091501 | 8/2007 |

OTHER PUBLICATIONS

Keller et al., Immunomodulator FTY720 Induces Myofibroblast Differentiation via the Lysophospholipid Receptor S1P3 and Smad3 Signaling, Am. J. Pathology, Jan. 2007, vol. 170, No. 1, pp. 281-292.
Yasuyuki Igarashi, Sphingosine-1-Phosphate as an Intercellular Signaling Molecule, Ann. NY Acad. Sci., 1998, vol. 845, pp. 19-31.
Jacobs et al., Intramuscular Interferon Beta-1a for Disease Progression in Relapsing Multiple Sclerosis, Ann. Neurol., 1996, vol. 39, No. 3, pp. 285-294.
Weinshenker et al., A Randomized Trial of Plasma Exchange in Acute Central Nervous System Inflammatory Demyelinating Disease, Ann. Neurol., 1999, vol. 46, No. 6, pp. 878-886.
Ganem et al., The Molecular Biology of the Hepatitis B Virus, Annu. Rev. Biochem., 1987, vol. 56 pp. 651-693.
Kaneko et al., Sphingosine-1-phosphate receptor agonists suppress concanavalin A-induced hepatic injury in mice, Biochem. and Biophys. Res. Commun., 2006, vol. 345, pp. 85-92.
Okazaki et al., Molecular Cloning of a Novel Putative G Protein-Coupled Receptor Expressed in the Cardiovascular System, Biochem. and Biophys. Res. Commun., 1993, vol. 190, No. 3, pp. 1104-1106.
Klein et al., Total Synthesis and Antifungal Evaluation of Cyclic Aminohexapeptides, Bioorg. Med. Chem., 2000, vol. 8, pp. 167-1696.
Hashimoto et al., β-Phenylselenoalanine as a dehydroalanine precursor-efficient synthesis of alternariolide (AM-toxin I), Chem. Commun., 1996, pp. 1139-1140.
Levkau et al., High-Density Lipoprotein Stimulates Myocardial Perfusion in Vivo, Circulation, 2004, vol. 110, pp. 3355-3359.
Salomone et al., S1P$_3$ receptors mediate the potent constriction of cerebral arteries by sphingosine-1-phosphate, Eur. J. Pharmacol., 2003, vol. 469, pp. 125-134.
Heneghan et al., Current and Novel Immunosuppressive Therapy for Autoimmune Hepatitis, Hepatology, 2002, vol. 35, No. 1, pp. 7-13.
Francis V. Chisari, Cytotoxic T Cells and Viral Hepatitis, J. Clin. Invest., Apr. 1997, vol. 99, No. 7, pp. 1472-1477.
Kiuchi et al., Synthesis and Immunosuppressive Activity of 2-Substituted 2-Aminopropane-1,3-diols and 2-Aminoethanols, J. Med. Chem., 2000, vol. 43, pp. 2946-2961.
Brinkmann et al., The Immune Modulator FTY720 Targets Sphingosine 1-Phosphate Receptors, J. Biol. Chem., 2002, vol. 277, No. 24, pp. 21453-21457.
Sanna et al., Sphingosine 1-Phosphate (S1P) Receptor Subtypes S1P$_1$ and S1P$_3$, Respectively, Regulate Lymphocyte Recirculation and Heart Rate, J. Biol. Chem., Apr. 2, 2004, vol. 279, No. 14, pp. 13839-13848.
Forrest et al., Immune Cell Regulation and Cardiovascular Effects of Sphingosine 1-Phosphate Receptor Agonists in Rodents are Mediated via Distinct Receptor Subtypes, J. Pharm. Exp. Ther., 2004, vol. 309, No. 2, pp. 758-768.
George C. Ebers, Randomised double-blind placebo-controlled study of interferon β-1a in relapsing/remitting multiple sclerosis, Lancet, Nov. 7, 1998, vol. 352, pp. 1498-1501.
Takuwa et al., Subtype-specific, differential activities of the EDG family receptors for sphingosine-1-phosphate, a novel lysophospholipid mediator, Mol. Cell. Endocrinol., 2001, vol. 177, pp. 3-11.
Fried et al., Peginterferon Alfa-2a Plus Ribavirin for Chronic Hepatitis C Virus Infection, N. Engl. J. Med., Sep. 26, 2002, vol. 347, No. 13, pp. 975-982.
Mailliard et al., Suppressing Hepatitis B without Resistance—So Far, So Good, N. Engl. J. Med., Feb. 27, 2003, vol. 348, No. 9, pp. 848-850.
Niessen et al., Dentritic cell PAR1-S1P3 signalling couples coagulation and inflammation, Nature, Apr. 3, 2008, vol. 452, No. 3, pp. 654-658.
IFNB Multiple Sclerosis Study Group, Interferon beta-1b is effective in relapsing-remitting multiple sclerosis. I. Clinical results of a multicenter, randomized, double-blind, placebo-controlled trial, Neurology, Apr. 1993, vol. 43, pp. 655-661.
Paty et al., Interferon beta-1b is effective in relapsing-remitting multiple sclerosis. II. MRI analysis results of a multicenter, randomized, double-blind, placebo-controlled trial, Neurology, Apr. 1993, vol. 43, pp. 662-667.
Johnson et al., Copolymer 1 reduces relapse rate and improves disability in relapsing-remitting multiple sclerosis: Results of a phase III multicenter, double-blind, placebo-controlled trial, Neurology, Jul. 1995, vol. 45, pp. 1268-1276.
Zivadinov et al., Effects of IV methylprednisolone on brain atrophy in relapsing-remitting MS, Neurology, 2001, vol. 57, pp. 1239-1247.
Goodin et al., Disease modifying therapies in multiple sclerosis; Report of the Therapeutics and Technology Assessment Subcommittee of the American Academy of Neurology and the MS Council for Clinical Practice Guidelines, Neurology, 2002, vol. 58, pp. 169-178.
Rudick et al., Management of Multiple Cclerosis, N. Engl. J. Med., Nov. 27, 1997, vol. 337, No. 22, pp. 1604-1611.

Daniel K. Podolsky, Inflammatory Bowel Disease, N. Engl. J. Med., Aug. 8, 2002, vol. 347, No. 6, pp. 417-429.

Kappos et al., Oral Fingolimod (FTY720) for Relapsing Multiple Sclerosis, N. Engl. J. Med., Sep. 14, 2006, vol. 355, No. 11, pp. 1124-1140.

Viscido et al., Inflammatory bowel diseases: clinical update of practical guidelines, Nucl. Med. Commun., 2005, vol. 26, No. 7, pp. 649-655.

Gon et al., S1P$_3$ receptor-induced reorganization of epithelial tight junctions comprises lung barrier integrity and is potentiated by TNF, PNAS, Jun. 28, 2005, vol. 102, No. 26, pp. 9270-9275.

Saito et al., Hepatitis C virus infection is associated with the development of hepatocellular carcinoma, Proc. Natl. Acad. Sci. USA, Sep. 1990, vol. 87, pp. 6547-6549.

Mandala et al., Alteration of Lymphocyte Trafficking by Sphingosine-1-Phosphate Receptor Agonists, Science, Apr. 2, 2002, vol. 296, pp. 346-349.

Hinterding et al., Synthesis of Chiral Analogues of FTY720 and its Phosphate, Synthesis, 2003, No. 11, pp. 1667-1670.

Campbell et al., The Synthesis of Novel Amino Acids via Hydroboration-Suzuki Cross Coupling, Tetrohedron Letters, 1999, vol. 40, pp. 5263-5266.

Collier et al., The direct synthesis of novel enantiomerically pure α-amino acids in protected form via suzuki cross-coupling, Tetrahedron Letters, 2000, vol. 41, pp. 7115-7119.

Long et al., Enantioselective syntheses of homophenylalanine derivatives via nitron 1,3-dipolar cycloaddition reactions with styrenes, Tetrahedron Letters, 2001, vol. 42, pp. 5343-5345.

International Search Report mailed Oct. 18, 2005 in International (PCT) Application No. PCT/JP2005/013113.

International Preliminary Report on Patentability issued Jan. 16, 2007 in International (PCT) Application No. PCT/JP2005/013113.

Shimizu et al., KRP-203, a Novel Synthetic Immunosuppressant, Prolongs Graft Survival and Attenuates Chronic Rejection in Rat Skin and Heart Allografts, Circulation, 2005, vol. 111, pp. 222-229.

Takahashi et al., A Novel Immunomodulator KRP-203 Combined with Cyclosporine Prolonged Graft Survival and Abrogated Transplant Vasculopathy in Rat Heart Allografts, Transplant. Proc., 2005, vol. 37, pp. 143-145.

* cited by examiner

EFFECTIVE USE METHOD OF MEDICAMENTS AND METHOD OF PREVENTING EXPRESSION OF SIDE EFFECT

This is a divisional of application Ser. No. 11/631,128, filed Feb. 20, 2007, now U.S. Pat. No. 7,781,617, which is a 371 application of International Application No. PCT/JP2005/013113, filed Jul. 15, 2005.

TECHNICAL FIELD

The present invention relates to medicaments comprising diaryl sulfide or diaryl ether compound having a 2-amino-1,3-propanediol structure having an activity of reducing lymphocytes circulating peripherally, in combination with an immunosuppressive agent and/or an anti-inflammatory agent, and also to methods which make immunosuppressive activity or anti-inflammatory activity effectively express and reduce expression of side effect.

BACKGROUND ART

Development of a method of suppressing immune response is very important for preventing rejection response in organ or cell transplantation, and treating and preventing various autoimmune diseases. Compounds that are conventionally used for suppression of immune response are based on either mechanism of action: (1) attacking a specific immune cell to remove the cell from the immune system, or (2) inhibiting the ability of an immune cell to respond to cytokine, thereby reducing the number of cells involved in immune response. As the number of responding cells reduces, the immune system is disabled to give a normal responding reaction, so that the immune response is suppressed.

To be more specific, the group of compounds based on the first mechanism of action will inhibit nucleotide synthesis in immune cells and stop metabolism and immune activity of the cells. This group includes azathioprine (Non-patent document 1), mizoribine (Non-patent document 2), mycophenolic acid (hereinafter, also abbreviated as "MPA," Non-patent document 3), brequinar sodium (Non-patent document 4), leflunomide, and methotrexate. However, these compounds face the problem that they are likely to cause toxic side effects.

The group of compounds based on the second mechanism of action includes cyclosporine A (hereinafter also abbreviated as "CsA"), tacrolimus (hereinafter also abbreviated as "FK506") and rapamycin (Non-patent document 5) and the like. These compounds will inhibit synthesis of cytokine such as IL-2, to thereby disable induction of proliferation and differentiation of effector cells and inhibit immune response. On the other hand, rapamycin blocks a cytokine signal from acting on an immune cell.

In order to mitigate side effects associated with individual immunosuppressive agents, therapies using either CsA or FK506, together with other immunosuppressive agent such as azathioprine or mizoribine or steroids (Non-patent document 6), (Non-patent document 7) or steroids have widely conducted, however, they do not always show sufficient immunosuppressive effect without representing toxic side effects.

As to an amino propanediol derivative having immunosuppressive activity, combinational effect of FTY720 and calcineurin inhibitor is known (Patent document 1). However, it is important to develop new agents for better expression of action or for reduction of side effect.

[Non-patent document 1] Nature, 183: 1682 (1959).
[Non-patent document 2] J. Clin. Invest., 87:940 (1991).
[Non-patent document 3] Pharm. Res., 7: 161 (1990).
[Non-patent document 4] Transplantation, 53: 303 (1992).
[Non-patent document 5] N. Eng. J. Med., 321:1725 (1989); Transplant. Proc., 23: 2977 (1991).
[Non-patent document 6] Transplant. Proc., 17: 1222 (1985).
[Non-patent document 7] Clin. Transplant., 4: 191 (1990).
[Patent document 1] Japanese Patent Laid-Open Publication No. Hei 11-80026

DISCLOSURE OF THE INVENTION

Problem to be Solved by the Invention

It is an object of the present invention to provide a method of efficiently eliciting effect of an immunosuppressive agent or an anti-inflammatory agent, i.e., immunosuppressive activity or anti-inflammatory activity at maximum while reducing side effect of the immunosuppressive agent or the anti-inflammatory agent by combinational use of an immunosuppressive agent or an anti-inflammatory agent known in the art which by itself has low toxicity and can be used with safety and without occurrence of side effect.

Means for Solving the Problem

The inventors of the present invention found that use of diaryl sulfide or diaryl ether compound having a 2-amino-1,3-propanediol structure having an activity of reducing lymphocytes circulating peripherally, in combination with other immunosuppressive agent or anti-inflammatory agent allows effective expression of immunosuppressive activity or anti-inflammatory activity of the combined agent and that side effects can be reduced by reducing an amount which is enough to express an effect of the combined agent, and finally accomplished the present invention.

Specifically, the present invention relates to:

1) A medicament comprising diaryl sulfide or diaryl ether compound having a 2-amino-1,3-propanediol structure having an activity of reducing lymphocytes circulating peripherally, in combination with an immunosuppressive agent and/or anti-inflammatory agent, 2) The medicament according to the above 1), wherein the diaryl sulfide or diaryl ether compound having a 2-amino-1,3-propanediol structure having an activity of reducing lymphocytes circulating peripherally is a compound represented by the general formula (1):

[Chemical formula 1]

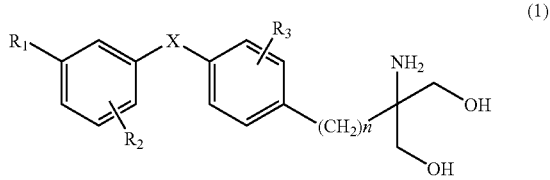

(1)

[wherein, $R_1$ represents a halogen atom, trihalomethyl group, hydroxy group, lower alkyl group having 1 to 7 carbon atoms, optionally substituted phenyl group, aralkyl group, lower alkoxy group having 1 to 4 carbon atoms, trifluoromethyloxy group, phenoxy group, cyclohexylmethyloxy group, optionally substituted aralkyloxy group, pyridylmethyloxy group, cinnamyloxy group, naphthylmethyloxy group, phenoxymethyl group, hydroxymethyl group, hydroxyethyl group, lower alkylthio group having 1 to 4 carbon atoms, lower alkylsulfinyl group having 1 to 4 carbon atoms, lower alkylsulfonyl group having 1 to 4 carbon atoms, benzylthio group, acetyl group, nitro group or cyano group, $R_2$ represents a hydrogen atom, halogen atom, trihalomethyl group, lower alkoxy group having 1 to 4 carbon atoms, lower alkyl group having 1 to 7 carbon atoms, phenethyl group or benzyloxy group, $R_3$ represents a hydrogen atom, halogen atom, trifluoromethyl group, lower alkoxy group having 1 to 4 carbon atoms, hydroxy group, benzyloxy group, lower alkyl group having 1 to 7 carbon atoms, phenyl group, lower alkoxymethyl group having 1 to 4 carbon atoms, or lower alkylthio group having 1 to 4 carbon atoms, X represents O, S, SO or $SO_2$, and n represents an integer of 1 to 4] or its pharmaceutically acceptable salt and hydrate, 3) The medicament according to the above 2), wherein the compound represented by the general formula (1) is 2-amino-2-[4-(3-benzyloxyphenylthio)-2-chlorophenyl]ethyl-1,3-propanediol, 4) The medicament according to the above 2), wherein the compound represented by the general formula (1) is 2-amino-2-[4-(3-benzyloxyphenylthio)-2-chlorophenyl]ethyl-1,3-propanediol hydrochloride, 5) The medicament according to the above 1), wherein the immunosuppressive agent is a calcineurin inhibitor, 6) The immunosuppressive agent according to the above 5), wherein the calcineurin inhibitor is cyclosporin A or tacrolimus, 7) The medicament according to the above 1), wherein the immunosuppressive agent is methotrexate or mycophenolic acid or mycophenolate mofetil, and 8) A method for preventing expression of side effect by applying a medicament comprising diaryl sulfide or diaryl ether compound having a 2-amino-1,3-propanediol structure having an activity of reducing lymphocytes circulating peripherally, in combination with immunosuppressive agent and/or anti-inflammatory agent, thereby mutually enhancing efficacies of these agents, and reducing use amounts.

EFFECT OF THE INVENTION

Although diaryl sulfide or diaryl ether compound having a 2-amino-1,3-propanediol structure having an ability to reduce lymphocytes circulating peripherally exerts excellent immunosuppressive effect by itself, combinational use with CsA or FK506 which is a calcineurin inhibitor mutually enhances immunosuppressive effects of these agents. As a result, a use amount of calcineurin inhibitor can be reduced, and limitation in clinical application due to renal toxicity or liver toxicity of CsA or FK506 can be disposed of, so that a safe and effective therapeutic method can be provided. Also combinational use with mycophenolic acid (MPA) having an activity of inhibiting nucleoside synthesis to stop metabolism and immune activity of immune cells allows mutual enhancement of immunosuppressive effects of both agents. This in turn reduces a use amount of MPA and avoids expression of digestive symptoms such as diarrhea or nausea, pancytopenia or neutropenia, secondary infection, or lymphoma, and provides safe and satisfactory therapy. Furthermore, the same applies to using the compound of the present invention in combination with methotrexate which is a first-line agent in therapy of rheumatoid arthritis. In other words, diaryl sulfide or diaryl ether compound having a 2-amino-1,3-propanediol structure having an activity of reducing lymphocytes circulating peripherally by itself exhibits excellent effect of suppressing occurrence of arthritis in an adjuvant arthritis model, however, when it is used in combination with methotrexate, their effects are mutually enhanced, and progression of arthritis can be suppressed by combination of smaller amounts of these agents. Methotrexate has strong side effects, so that low-level pulse therapy is employed in therapy of rheumatoid arthritis. However, according to the method of the present application, dose of methotrexate can be reduced, and a safe therapeutic method capable of avoiding side effects can be provided. In brief, since methotrexate expresses its effect in a small amount, the agent can be used safely over a prolonged period, and efficient and sustained suppression of progression and recurrence of condition of rheumatoid arthritis is expected.

BEST MODE FOR CARRYING OUT THE INVENTION

Figure 1:
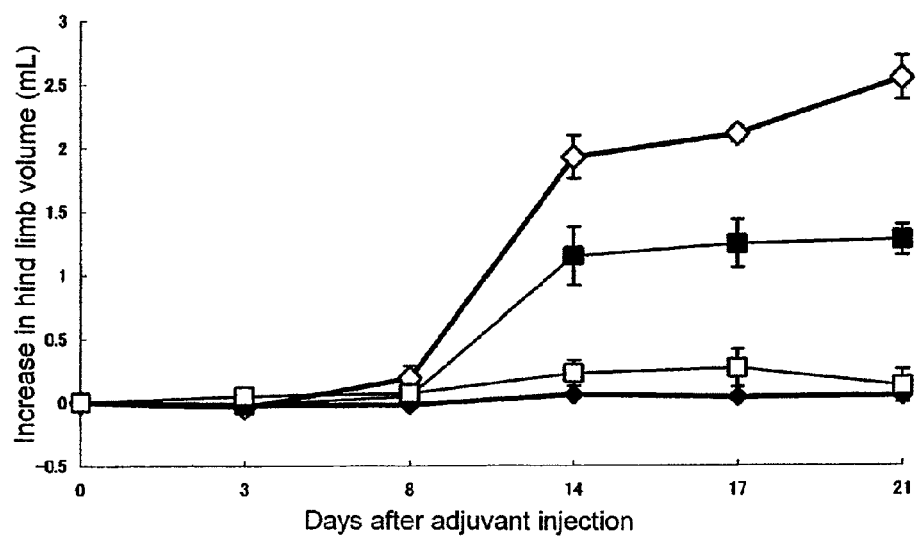
FIG. 1 Graph showing effect of single use of KNF-299 in rat adjuvant arthritis
◆: normal control
◇: adjuvant control
solid square: KNF-299 0.03 mg/kg.p.o.
□: KNF-299 0.1 mg/kg.p.o.

The diaryl sulfide or diaryl ether compound having a 2-amino-1,3-propanediol structure having an activity of reducing lymphocytes circulating peripherally of the present invention is a compound represented by the general formula (1):

[Chemical formula 2]

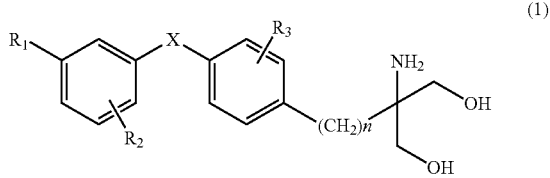

[wherein, $R_1$ represents a halogen atom, trihalomethyl group, hydroxy group, lower alkyl group having 1 to 7 carbon atoms, optionally substituted phenyl group, aralkyl group, lower alkoxy group having 1 to 4 carbon atoms, trifluoromethyloxy group, phenoxy group, cyclohexylmethyloxy group, optionally substituted aralkyloxy group, pyridylmethyloxy group, cinnamyloxy group, naphthylmethyloxy group, phenoxymethyl group, hydroxymethyl group, hydroxyethyl group, lower alkylthio group having 1 to 4 carbon atoms, lower alkylsulfinyl group having 1 to 4 carbon atoms, lower alkylsulfonyl group having 1 to 4 carbon atoms, benzylthio group, acetyl group, nitro group or cyano group, $R_2$ represents a hydrogen atom, halogen atom, trihalomethyl group, lower alkoxy group having 1 to 4 carbon atoms, lower alkyl group having 1 to 7 carbon atoms, phenethyl group or benzyloxy group, $R_3$ represents a hydrogen atom, halogen atom, trifluoromethyl group, lower alkoxy group having 1 to 4 carbon atoms, hydroxy group, benzyloxy group, lower alkyl group having 1 to 7 carbon atoms, phenyl group, lower alkoxymethyl group having 1 to 4 carbon atoms, or lower alkylthio group having 1 to 4 carbon atoms, X represents O, S, SO or $SO_2$, and n represents an integer of 1 to 4] or its pharmaceutically acceptable salt and hydrate.

As a pharmaceutically acceptable salt of compound represented by the general formula (1), hydrochloric acid salt, hydrobromic acid salt, acetic acid salt, trifluoroacetic acid salt, methane sulfonic acid salt, citric acid salt, tartaric acid salt and the like acid addition salts can be exemplified.

In the general formula (1) of the present invention, "halogen atom" represents fluorine atom, chlorine atom, bromine atom or iodine atom, "trihalomethyl group" represents trifluoromethyl group or trichloromethyl group, "lower alkyl group having 1 to 7 carbon atoms" includes straight chain or branched chain hydrocarbons having 1 to 7 carbon atoms such as methyl, ethyl, propyl, isopropyl, butyl, t-butyl, pentyl, hexyl, heptyl and the like. "Optionally substituted phenoxy group" includes those having at a certain position on a benzene ring, a halogen atom such as fluorine atom, chlorine atom, bromine atom or iodine atom, trifluoromethyl group, lower alkyl group having 1 to 4 carbon atoms, and lower alkoxy group having 1 to 4 carbon atoms. The term "aralkyl group" used in "aralkyl group" and "aralkyloxy group" represents benzyl group, diphenylmethyl group, phenethyl group or phenylpropyl group. The term "lower alkyl group" for "lower alkoxy group having 1 to 4 carbon atoms", "lower alkylthio group having 1 to 4 carbon atoms", "lower alkylsulfinyl group having 1 to 4 carbon atoms" and "lower alkylsulfonyl group having 1 to 4 carbon atoms" represents straight chain or branched chain hydrocarbon having 1 to 4 carbon atoms, e.g., methyl, ethyl, propyl, isopropyl, butyl and the like, and "optionally substituted aralkyl group" includes those having at a certain position on a benzene ring, a halogen atom such as fluorine atom, chlorine atom, bromine atom or iodine atom, trifluoromethyl group, lower alkyl group having 1 to 4 carbon atoms, and lower alkoxy group having 1 to 4 carbon atoms.

More specifically, 2-amino-2-[4-(3-benzyloxyphenylthio)-2-chlorophenyl]ethyl-1,3-propanediol or its hydrochloric acid salt can be exemplified.

The compound represented by the general formula (1) of the present invention is disclosed in, for example, WO03/029184 and WO03/029205, and may be produced in a method described in these publications.

The present invention exerts the effect in combinational use with an immunosuppressive agent and/or an agent having anti-inflammatory activity. The immunosuppressive agent of the present invention excludes diaryl sulfide or diaryl ether compound having a 2-amino-1,3-propanediol structure having an activity of reducing lymphocytes circulating peripherally.

As an agent that may be used in combination, immunosuppressive agents having immunosuppressive or immunoregulatory activity used for treatment or prophylaxis of acute or chronic rejection of allograft or heterograft, inflammatory diseases, autoimmune diseases, and/or anti-inflammatory agents having anti-inflammatory activity or malignant cell proliferation suppressing activity can be exemplified.

Concrete examples include CsA and FK506 which are calcineurin inhibitors, rapamycin, 40-O-(2-hydroxymethyl)-rapamycin, CCI779, ABT578 which are mTOR inhibitors, ascomycins having immunosuppressive activity such as ABT-281, ASM981 and mycophenolic acid (MPA), mycophenolate mofetil, azathioprine, mizoribine, and cyclosphosphamide. Also, methotrexate which is a folic acid metabolism antagonist, corticosteroid exhibiting wide anti-inflammatory activity, auranofin, actarit, mesalazine or sulfasalazine having immunoregulatory activity, infliximab which is anti-TNF-α antibody, MRA which is anti IL-6 receptor antibody, and natalizumab which is anti-integrin antibody can be exemplified.

In the case of combinational use, they may be administered to a patient separately or concurrently. Administration may be conducted in mixture or by itself. Dose form of compound is variable depending on the nature of the compound, and for example, an oral preparation or a parenteral preparation may be prepared. In other words, active ingredients may be admixed separately or concurrently with a physiologically acceptable carrier, excipient, binder, diluent and the like to prepare granule, powder, tablet, capsule, syrup, suppository, suspension, solution or the like preparation for oral or parenteral administration. When active ingredients are separately made into preparations, they may be administered after mixing just before administration, or may be administered simultaneously or successively at a certain time interval to the same patient. Preparations for such combination are produced in a routine technique.

Dose of each active ingredient used in combination is variable depending on various active ingredients to be contained, administration manner or condition to be treated. Typically, when a compound represented by the general formula (1) is used in combination with, for example, CsA and FK506 which are calcineurin inhibitors, rapamycin, 40-O-(2-hydroxymethyl)-rapamycin, CCI779, ABT578 which are mTOR inhibitors, ascomycins having immunosuppressive activity such as ABT-281, ASM981 and mycophenolic acid (MPA) or the like, a dose of 0.01 mg to 100 mg (day/adult) may be administered at once or in several times. Also when it is used in combination with methotrexate which is folic acid metabolism antagonist, a dose of 0.01 mg to 100 mg (day/adult) may be administered at once or in several times.

The immunosuppressive agent of the present invention obtained in this manner is useful for prophylaxis or treatment of resistance or transplantation rejection against transplantation of organ or tissue (for example, heart, kidney, liver, lung, bone marrow, cornea, pancreas, small intestine, limb, muscle, nerve, fatty marrow, duodenum, skin or pancreatic islet cell, including heterograft), graft-versus-host reaction (GVHD) caused by bone marrow transplantation, autoimmune diseases such as rheumatoid arthritis, systemic lupus erythematosus, nephrotic syndrome, Hashimoto's thyroiditis, multiple sclerosis, myasthenia gravis, type I diabetes, type II adult-onset type diabetes, uveitis, steroid-dependent and steroid-resistant nephrosis, palmoplantar pustulosis, allergic encephalomyelitis, glomerulonephritis and the like, as well as inflammation caused by pathogenic microorganism.

They are useful for prophylaxis and treatment of inflammatory, proliferative and hyper-proliferative skin diseases and immunity-mediated skin diseases appearing in skin, such as psoriasis, psoriatic arthritis, atopic eczema (atopic dermatitis), contact dermatitis, and further, eczematous dermatitis, seborrheic dermatitis, lichen planus, pemphigus, bullous pemphigoid, epidermolysis bullosa, urticaria, vascular edema, skin allergic antiitis, erythema, skin eosinophilia, acne, alopecia areata, eosinophilic fasciitis and atherosclerosis.

The present invention is also useful for treatment of respiratory diseases, such as sarcoidosis, pulmonary fibrosis, idiopathic interstitial pneumonia and reversible obstructive airway diseases, represented by bronchial asthma, bronchitis and the like.

Furthermore, the present invention may also be useful for treatment of ocular diseases, such as conjunctivitis, keratoconjunctivitis, keratitis, vernal conjunctivitis, Behcet's disease-associated uveitis, herpetic keratitis, keratoconus, corneal epithelial dystrophy, corneal leukoma, ocular pemphigus, Mooren's ulcer, scleritis, Basedow's disease-associated opthalmoplegia, severe intraocular inflammation and the like.

The present invention is also useful for prophylaxis and treatment of mucosal or vascular inflammations (e.g., gastric ulcer, vascular damage caused by ischemic disease and thrombus, ischemic bowel disease, inflammatory bowel diseases (e.g., Crohn's disease and ulcerative colitis), necrotizing colitis) or thermal burn-related intestinal injury.

Further, the present invention is also useful for prophylaxis and treatment of renal diseases (e.g., interstitial nephritis, Goodpasture's syndrome, hemolytic uremic syndrome and diabetic nephropathy), nervous diseases (such as polymyositis, Guillain-Barre syndrome, Meniere's disease and radiculopathy), endocrine diseases (such as hyperthyroidism and Basedow's disease), hemopathy (such as aplastic anemia, hypoplastic anemia, essential thrombocytopenic purpura, autoimmune hemolytic anemia, defective production of granulocytopenia and erythrocyte), bone diseases (such as osteoporosis), respiratory diseases (such as sarcoidosis, pulmonary fibrosis and idiopathic interstitial pneumonia), skin diseases (such as dermatomyositis, vitiligo vulgaris, ichthyosis vulgaris, photoallergic sensitivity and cutaneous T-cell lymphoma), circulatory diseases (such as arteriosclerosis, aortitis, polyarteritis nodosa and cardiac myopathy), collagen diseases (such as scleroderma, Wegener's granulomatosis and Sjogren's syndrome), adiposis, eosinophilic fasciitis, gum disease, nephrotic syndrome, hemolytic uremic syndrome, and muscular dystrophy.

The present invention may also be useful for treatment of bowel inflammation or allergy (celiac disease, proctitis, eosinophilic gastroenteritis, mastocytosis, Crohn's disease and ulcerative colitis), and allergosis, which are related to foodstuff but show symptoms not directly related to the gastrointestinal tract (e.g., migraine, rhinitis and eczema).

The present invention has an activity of promoting liver regeneration activity and/or thickening and overgrowth of hepatocytes. Therefore, the present invention is also useful for prophylaxis and treatment of immunogenic diseases (e.g., chronic autoimmune liver diseases including autoimmune hepatitis, primary biliary cirrhosis and sclerosing cholangitis), partial liver resection, acute liver necrosis (e.g., necrosis due to toxin, viral hepatitis, shock or oxygen depletion), and liver diseases such as hepatitis type B, hepatitis type C and liver cirrhosis.

Further, the present invention may also be useful for prophylaxis and treatment of malignant rheumatoid arthritis, amyloidosis, fulminant hepatitis, Shy-Drager syndrome, pustular psoriasis, Behcet's disease, systemic lupus erythematosus, endocrine ophthalmopathy, progressive systemic sclerosis, mixed connective tissue disease, aortitis syndrome, Wegener's granuloma, active chronic hepatitis, Evans' syndrome, hay fever, idiopathic hypoparathyroidism, Addison's disease (autoimmune adrenalitis), autoimmune orchitis, autoimmune ovaritis, cold hemagglutinin disease, paroxysmal cold hemoglobinuria, pernicious anemia, adult T cell leukemia, autoimmune atrophic gastritis, lupoid hepatitis, tubulointerstitial nephritis, membranous nephropathy, amyotrophic lateral sclerosis, rheumatic fever, post-myocardial infarction syndrome and sympathetic ophthalmia.

EXAMPLES

In the following, the present invention will be concretely explained by way of examples. In these examples, among compounds represented by the general formula, combinations of 2-amino-2-[4-(3-benzyloxyphenylthio)-2-chlorophenyl]ethyl-1,3-propanediol (hereinafter, abbreviated as "KNF-299") and cyclosporin A (CsA), tacrolimus (FK506), methotrexate (MTX) and mycophenolic acid (MPA) will be particularly described, however, it is to be understood that the present invention will never be limited to these examples.

Example 1

Prolonging Effect on Skin Allograft Survival Between Major Histocompatibility Complex (MHC) Compatible Rat Strains Allogeneic skin transplantation between MHC-compatible rats was conducted in the manner as described below with reference to, for example, the literatures (A.m. J. Med. Technol.; 36, 149-157, 1970, Transplant. Proc.; 28, 1056-1059, 1996). Five animals were included per group, and all rats were bread in separate cages. LEW($RT1^l$) was selected as donor, and F344($RT1^{lvl}$) was selected as recipient. A part of dermis (1.8×1.8 cm) on the back of recipient was excised, and after giving several drops of penicillin solution (40,000 U/mL, in saline) thereon, a full thickness skin graft (1.8×1.8 cm) prepared from abdominal part of donor was put thereon. First-aid adhesive tape (30×72 mm) was applied so that the center pad thereof lies on the graft, and secured by binding aeration tape (adhesive bandage, 3.8×15 cm) therearound. At 5 days, the first-aid adhesive tape and the aeration tape were removed by cutting with scissors.

Drug administration was conducted by orally administering 0.5 mL/100 g B.W. of drug once a day everyday from the day of skin transplantation. Control group was received distilled water. As the CsA, Sandimmun injection (50 mg/mL) diluted in distilled water was administered. As the FK506, the filling of Prograf capsule (Fujisawa Pharmaceutical Co., Ltd.) suspended in distilled water was administered. KNF-299 was administered after being dissolved in distilled water. A combinational administration group was received a mixture prepared by mixing liquids to be administered right before administration.

Grafts were observed everyday from fifth day of transplantation at which the first-aid adhesive tape was removed, and the condition that 90% or more of graft epithelium necrotized to turn brown was determined as occurrence of rejection. Number of days from transplantation to determination of rejection was defined as a survival time.

Mean value of survival times for each group was calculated as a mean survival time (MST). In each group (n=5), the third-longest survival time was defined as a median value.

KNF-299 showed the prolonging effect on the mean survival time for 27 days or more by single administration of 3 mg/kg. Prolonging effect on survival for 30 days or more was observed by single administrations of CsA and FK506 in doses of 30 mg/kg and 10 mg/kg, respectively.

Table 1 shows results of the test for demonstrating combinational use effect using a dose which is smaller than the dose at which survival prolonging effect was observed in single administration.

KNF-299 showed clear prolonging effect on graft survival in single administration of 3 mg/kg. Also CsA showed clear survival prolonging effect in single administration of 30 mg/kg. Dosages of CsA 10 mg/kg and KNF-299 0.03 mg/kg merely resulted in about 1 to 4 days prolonging of survival compared to control, however, when they are used in combination, 30 days or longer prolonging of survival was observed in every case, and excellent rejection suppressing effect was induced. The combination with FK506 gave similar results, and little effect was observed in single administration of low dose, however, the combinational use group of FK506 3 mg/kg and NF-299 0.1 mg/kg showed a clear combinational effect as is evident from a mean survival time of 26 days or longer.

TABLE 1

Prolonging effect on skin allograft survival between MHC-compatible rat

| Compound (mg/kg, oral administration) | N | Survival time (day) of skin graft Individual survival day | MST | Median |
|---|---|---|---|---|
| Test 1 | | | | |
| Control | 5 | 8, 9, 9, 9, 10 | 9.0 | 9.0 |
| KNF-299 (3) | 5 | 17, >30, >30, >30, >30 | >27.4 | >30 |
| CsA (30) | 4 | >30, >30, >30, >30 | >30 | >30 |
| Test 2 | | | | |
| Control | 5 | 7, 8, 8, 8, 9, 9 | 8.0 | 8.0 |
| CsA (10) | 5 | 9, 11, 12, 13, 14 | 11.8 | 12.0 |
| KNF-299 (0.03) | 5 | 8, 9, 9, 9, 10 | 9.0 | 9.0 |
| CsA(10) + KNF-299(0.03) | 4 | >30, >30, >30, >30 | >30 | >30 |
| Test 2 | | | | |
| Control | 5 | 7, 7, 8, 9, 9 | 8.0 | 8.0 |
| FK506 (3) | 5 | 9, 9, 9, 9, 10 | 9.2 | 9.0 |
| KNF-299 (0.1) | 5 | 8, 8, 9, 9, 10 | 8.8 | 9.0 |
| FK506(3) + KNF-299(0.1) | 5 | 13, >30, >30, >30, >30 | >26.6 | >30 |

As described above, it was demonstrated that combinational use of KNF-299 enhances the effect of a calcineurin inhibitor such as CsA or FK506. Since the use amount of the calcineurin inhibitor can be reduced, the possibility of eliminating limitation in clinical application due to expression of renal toxicity or liver toxicity, and an effective therapeutic method is provided.

Example 2

Effect of Combined Use with Methotrexate (MTX) in Rat Adjuvant Arthritis (AA) Model In a footpad of right hind limb of 6 or 7-week-old female LEW/Crj rat (Charles River Japan, Inc.), 0.05 mL (0.6 mg/animal) of killed *M. butyricum* (12 mg/mL) suspended in liquid paraffin was intradermally injected to cause arthritis (Day 0). Test compound was dissolved or suspended in pure water and orally administered in a volume of 0.5 mL per 100 g of body weight of rat. Adjuvant control was received only pure water. As for the combinational administration group, an aqueous solution of KNF-299 and an aqueous solution of MTX(Sigma) were administered after being mixed before administration. Administration was conducted once a day everyday from Day 0 to end of the experiment.

Evaluation of arthritis was made by measuring volumes of left and right hind limbs by using a volume meter (MK-550, Muromachi Kikai) at Day 0, 3, 8, 14, 17, and 21, and determining an increase relative to hind limb at Day 0.

Figure 2:
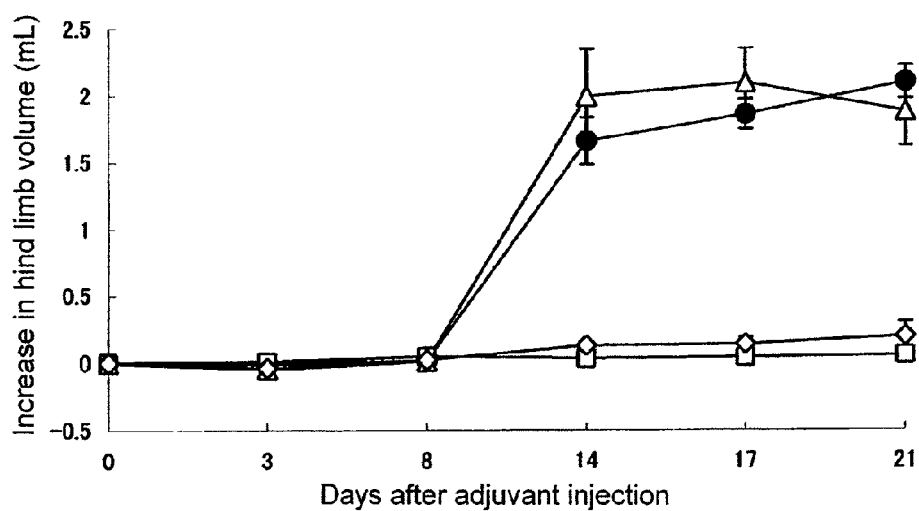
FIG. 2 Graph showing effect of single use of methotrexate (MTX) in rat adjuvant arthritis
●: adjuvant control
□: normal control
Δ: MTX 0.03 mg/kg
◇: MTX 0.1 mg/kg
FIG. 3 Graph showing effect of combinational use of KNF-299 and MTX in rat adjuvant arthritis
○: adjuvant control
Δ: KNF-299 0.01 mg/kg
□: MTX 0.025 mg/kg
◇: MTX 0.05 mg/kg
solid square: KNF-299 (0.01 mg/kg)+MTX (0.025 mg/kg)
◆: KNF-299 (0.01 mg/kg)+MTX (0.05 mg/kg)

The ability of KNF-299 to prevent onset of adjuvant arthritis is dose dependent and reaches almost maximum at 0.1 mg/kg (FIG. 1). The ability of MTX to prevent onset was not observed at 0.03 mg/kg, and reached maximum at 0.1 mg/kg (FIG. 2).

Figure 3:
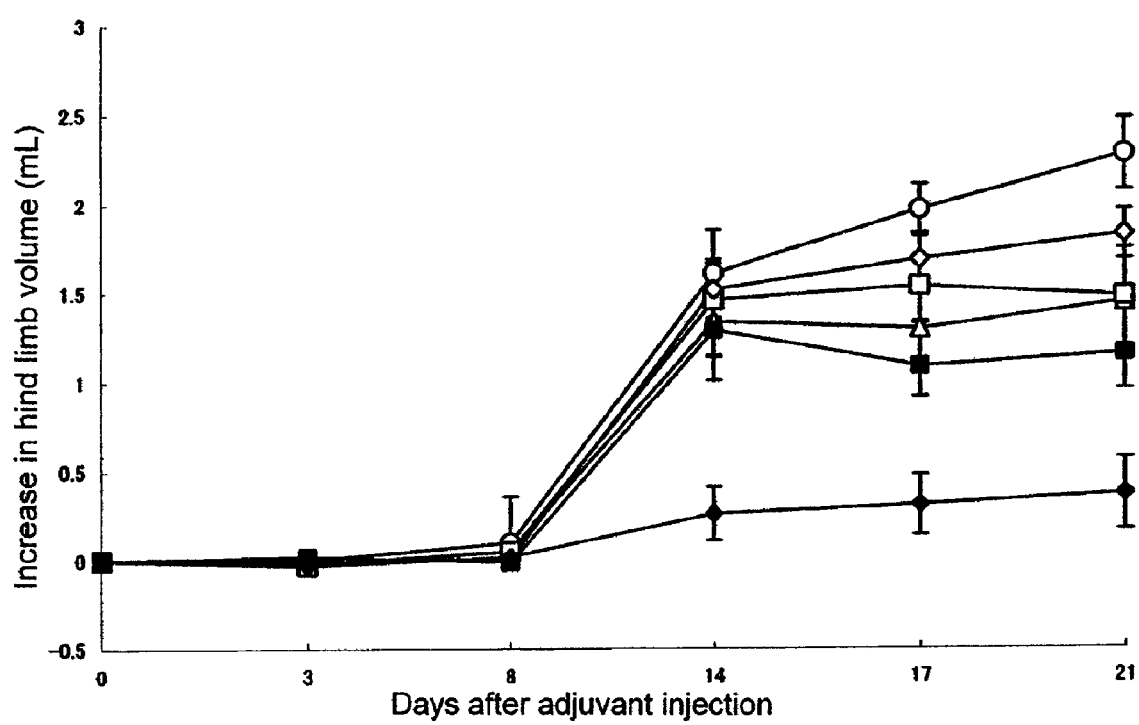

Combinational effect was examined for a combination of doses with which little effect was expected in single administrations. Dose of KNF-299 was 0.01 mg/kg and dose of MTX was 0.025 mg/kg and 0.05 mg/kg. Results are shown in FIG. 3.

MTX showed 20% and 35% inhibition in single administrations of 0.025 mg/kg and 0.05 mg/kg, respectively, however the effect was not significant (Day 21). KNF-299 showed 36% (Day 21) inhibition in single administration of 0.01 mg/kg. Combinational use of 0.01 mg/kg of KNF-299, and MTX presented an effect of combinational use, and combinational use with 0.05 mg/kg of MTX showed 84% inhibition.

MTX is a folic acid metabolism antagonist, and is known to cause myelosuppression, interstitial pneumonia and the like side effects. KNF-299 was demonstrated that it exhibits excellent combinational effect on AA model by combinational use with MTX which has the best clinical efficacy and hence is a first-line therapy. Therefore, combinational use of KNF-299 would be effective on a patient suffering from intractable rheumatoid arthritis for which effect of MTX is difficult to appear. MTX has strong side effects, so that low-level pulse therapy is employed in therapy of rheumatoid arthritis. Also in this case, a side effect may occur, and thus folic acid is used in combination to mitigate such side effect. Combinational use of KNF-299 with MTX allows reduction in dose amounts of MTX and KNF-299, and prevents side effects, and enables provision of a safe therapeutic method.

Example 3

Prolonging Effect of Combinational Use with Mycophenolic Acid (MPA) on Survival of Heart Graft Between Major Histocompatibility Complex (MHC) Incompatible Rat Strains Effect of KNF-299 was examined in allogeneic heart transplantation between MHC-incompatible rats. Using combination of DA (RT1$^a$) rat as a donor, and LEW (RT1$^l$) rat as a recipient, heterotopic heart transplantation in which heart of donor is joined to neck vessel of recipient with a cuff was conducted with reference to a literature (Microsurgery; 21, 16-21, 2001) or the like.

Drug was administered orally once a day everyday from the day of heart transplantation. MPA was prepared from the product purchased from Wako Pure Chemical Industries, Ltd. so that the concentration was 20 mg/mL in a saline containing 0.5% carboxymethyl cellulose, 0.4% Tween 80, and 0.9% benzyl alcohol, and administered in 0.1 mL/100 g B.W.

KNF-299 was dissolved in distilled water in a concentration of 0.06 mg/mL, and administered in 0.5 mL/100 g B.W. A control group was received a vehicle used for MPA administration liquid.

Cardiac pulsation of the transplanted heart was checked by inspection or palpation, and determination of rejection was made when cardiac pulsation stopped. Number of days from transplantation to determination of rejection was defined as survival time. Mean value of survival time in each group was calculated as mean survival time (MST). Table 2 shows results of the test for demonstrating preventing effect on rejection of transplanted heart using a combination of strains that showed strong rejection.

TABLE 2

Prolonging effect on heart graft survival between MHC-incompatible rat strains

| Compound (mg/kg, oral administration) | N | Survival time (day) of transplanted heart | |
|---|---|---|---|
| | | Individual survival day | MST |
| Control | 5 | 5, 6, 6, 6, 6 | 5.8 |
| MPA (20) | 7 | 18, 26, 34, 50, 53, >100, >100 | >54.4 |
| KNF-299 (0.3) | 5 | 6, 7, 7, 7, 8 | 7.0 |
| MPA (20) + KNF-299 (0.3) | 6 | >100, >100, >100, >100, >100, >100 | >100 |

In single administration of 0.3 mg/kg of KNF-299, the mean survival time was 7.0 days, and only a small prolonging effect of 1.2 days compared to control group was observed. In single administration of 20 mg/kg of MPA, individual variability in survival time was large and rejection preventing effect was insufficient in spite of high dose. When they are used in combination, survival time was prolonged by 100 days or longer in every case, which revealed clear combinational use effect.

INDUSTRIAL APPLICABILITY

In organ transplantations, diaryl sulfide or diaryl ether compound having a 2-amino-1,3-propanediol structure having an activity of reducing lymphocytes circulating peripherally exerts excellent immunosuppressive effect by itself, however, combinational use of an immunosuppressive agent such as CsA or FK506 which is a calcineurin inhibitor, or mycophenolic acid (MPA) which is a nucleoside synthesis inhibitor or combinational use of an anti-inflammatory agent enhances the effect. Therefore, clinical doses of CsA, FK506, mycophenolate mofetil can be reduced, and hence limitation in using calcineurin inhibitors due to renal toxicity or liver toxicity, or limitation in using nucleoside synthesis inhibitors due to neutrophil depletion can be avoided, so that a safe and effective therapeutic method can be provided. Also in therapy of rheumatoid arthritis, dose of methotrexate can be reduced according to the method of the present application, so that a safe therapeutic method avoiding side effects can be provided. In brief, since the agents used in combination express sufficient anti-inflammatory effect with small amounts, such agents can be used safely over a prolonged period, and hence efficient and sustained suppression of progression and recurrence of condition of rheumatoid arthritis is expected.

Therefore, the medicament of the present invention comprising diaryl sulfide or diaryl ether compound having a 2-amino-1,3-propanediol structure having an activity of reducing lymphocytes circulating peripherally, in combination with an immunosuppressive agent and/or an anti-inflammatory agent is useful as a measure for effectively expressing immunosuppressive activity or anti-inflammatory activity and reducing expression of side effect. Such a medicament is useful for prophylaxis and treatment of autoimmune diseases and inflammations caused by pathogenic microorganisms, foreign antigens or foreign substances, as well as for prophylaxis and treatment of inflammatory, proliferative and hyperproliferative skin diseases and immunogen-mediated diseases appearing in skin.

The invention claimed is:

1. A method for treating an autoimmune disease, comprising administering to a subject in need thereof a therapeutically effective amount of a medicament comprising a diaryl sulfide or diaryl ether compound having a 2-amino-1,3-propanediol structure having an activity of reducing lymphocytes circulating peripherally, wherein the compound is represented by formula (1):

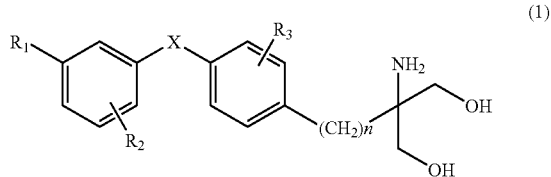

wherein:
$R_1$ represents a halogen atom, trihalomethyl group, hydroxy group, lower alkyl group having 1 to 7 carbon atoms, optionally substituted phenyl group, aralkyl group, lower alkoxy group having 1 to 4 carbon atoms, trifluoromethyloxy group, phenoxy group, cyclohexylmethyloxy group, optionally substituted aralkyloxy group, pyridylmethyloxy group, cinnamyloxy group, naphthylmethyloxy group, phenoxymethyl group, hydroxymethyl group, hydroxyethyl group, lower alkylthio group having 1 to 4 carbon atoms, lower alkylsulfinyl group having 1 to 4 carbon atoms, lower alkylsulfonyl group having 1 to 4 carbon atoms, benzylthio group, acetyl group, nitro group or cyano group, $R_2$ represents a hydrogen atom, halogen atom, trihalomethyl group, lower alkoxy group having 1 to 4 carbon atoms, lower alkyl group having 1 to 7 carbon atoms, phenethyl group or benzyloxy group, $R_3$ represents a hydrogen atom, halogen atom, trifluoromethyl group, lower alkoxy group having 1 to 4 carbon atoms, hydroxy group, benzyloxy group, lower alkyl group having 1 to 7 carbon atoms, phenyl group, lower alkoxymethyl group having 1 to 4 carbon atoms, or lower alkylthio group having 1 to 4 carbon atoms, X represents O, S, SO or $SO_2$, and n represents an integer of 1 to 4, or its pharmaceutically acceptable salt or hydrate, in combination with an additional immunosuppressive agent.

2. The method according to claim 1, wherein the autoimmune disease is selected from the group consisting of rheumatoid arthritis, systemic lupus erythematosus, nephrotic syndrome, Hashimoto's thyroiditis, multiple sclerosis, myasthenia gravis, type I diabetes, type II adult-onset type diabetes, uveitis, steroid-dependent and steroid-resistant nephrosis, palmoplantar pustulosis, allergic encephalomyelitis, glomerulonephritis and inflammatory bowel disease.

3. The method according to claim 1, wherein the autoimmune disease is rheumatoid arthritis, multiple sclerosis or inflammatory bowel disease.

4. The method according to claim 1, wherein the compound represented by formula (1) is 2-amino-2-[4-(3-benzyloxyphenylthio)-2-chlorophenyl]ethyl-1,3-propanediol.

5. The method according to claim 1, wherein the compound represented by formula (1) is 2-amino-2-[4-(3-benzyloxyphenylthio)-2-chlorophenyl]ethyl-1,3-propanediol hydrochloride.

6. The method according to claim 5, wherein the additional immunosuppressive agent is a calcineurin inhibitor.

7. The method according to claim 6, wherein the calcineurin inhibitor is cyclosporin A or tacrolimus.

* * * * *